(12) United States Patent
Hata et al.

(10) Patent No.: US 6,296,881 B1
(45) Date of Patent: Oct. 2, 2001

(54) BACTERICIDE CONTAINING IRON IONS

(75) Inventors: Tadayo Hata, Osaka; Toshiyuki Maruoka, Toyonaka, both of (JP)

(73) Assignee: Kenkohyakunijussai Co., Ltd., Osaka (JP)

( * ) Notice: Subject to any disclaimer, the term of this patent is extended or adjusted under 35 U.S.C. 154(b) by 0 days.

(21) Appl. No.: 09/365,822

(22) Filed: Aug. 3, 1999

(30) Foreign Application Priority Data

Aug. 3, 1998 (JP) ................................................... 10-219269

(51) Int. Cl.⁷ .......................... A01N 59/16; A01N 37/00; A01N 43/08; A01N 55/02
(52) U.S. Cl. .......................... 424/647; 424/646; 514/474; 514/502; 514/532; 514/557; 514/576; 514/578
(58) Field of Search ..................................... 424/646, 647; 514/502, 474, 532, 557, 576, 578

(56) References Cited

U.S. PATENT DOCUMENTS 3,404,987 * 10/1968 Kooistra et al. .......................... 426/9
5,389,391 * 2/1995 Monte .................................. 426/335

FOREIGN PATENT DOCUMENTS 0 608 944 * 8/1994 (EP) .

* cited by examiner

*Primary Examiner*—Jose' G. Dees
*Assistant Examiner*—Frank Choi
(74) *Attorney, Agent, or Firm*—Armstrong, Westerman, Hattori, McLeland & Naughton, LLP

(57) ABSTRACT

Pathogenic bacteria have long posed a threat to mankind, and it has been a goal in the food industry and the medical profession to develop a bactericide that would have a high degree of practicality which included spores in its scope, that would exhibit a pronounced effect on pathogenic bacteria, that would be safe for humans and the earth, and that would be composed of metal ions having affinity with the body, that is, those which are essential structural components for the body, and compounds that are used in food additives. Provided are a bactericide containing ferric ions ($Fe^{3+}$) and one or more members of the group consisting of sorbic acid, benzoic acid, and para-hydroxybenzoic acid esters; a bactericide containing ferric ions ($Fe^{3+}$), L-ascorbic acid, and one or more members of the group consisting of sorbic acid, benzoic acid, and para-hydroxybenzoic acid esters; and a bactericide containing ferric ions ($Fe^{3+}$), sorbic acid, benzoic acid, and L-ascorbic acid. As a result, the major pathogenic bacteria can be eradicated in a short time, and the bactericide is highly stable.

1 Claim, 1 Drawing Sheet

BACTERICIDE CONTAINING IRON IONS

BACKGROUND OF THE INVENTION

1. Field of the Invention

The present invention relates to a bactericide containing ferric ions ($Fe^{3+}$) and one or more members of the group consisting of sorbic acid, benzoic acid, and para-hydroxybenzoic acid esters, and to a bactericide containing ferric ions ($Fe^{3+}$), L-ascorbic acid, and one or more members of the group consisting of sorbic acid, benzoic acid, and para-hydroxybenzoic acid esters, which can be used in a wide range of applications, from the sterilization of hands and wounds, to the sterilization of furniture, tools, and objects, to the sterilization of fresh foods prior to cooking.

2. Description of the Related Art

Despite the sophisticated roadway system and communication network, huge budgets, numerous CDC (Center for Disease Control) personnel, and state-of-the-art medical treatment available in a developed country like the United States, and even though it has been 16 years since the discovery of *Escherichia coli* O-157, there are still more than 20,000 new patients each year, and over 200 deaths. In Japan as well, there were numerous mass infections in 1996, and at the present time the situation is still far from static, to the extent that there are researchers who say that this O-157 is a "microbe" that can survive anywhere in the environment and causes infection at a very low bacterium count, and furthermore it is a known fact that there is no way to halt the onslaught of tubercule bacilli or staphylococci with resistance to multiple drugs.

Moreover, in developing countries, oral infectious diseases such as dysentery and cholera are as rampant as ever, and respiratory infectious diseases such as tuberculosis are also widespread. There are currently twenty million patients with tuberculosis in the world, and while most of these are in Africa and other developing countries, there are eight million new cases each year, and the annual number of deaths is said to be in excess of three million. While ignorance about infectious diseases and poor public sanitation cannot be overlooked, these facts are probably also attributable to the fact that people have no antiseptic that allows instantaneous disinfection and is very safe.

Of the sterilization and disinfection methods in daily use today, alcohols, phenols, halogen compounds, quaternary ammonium salts, biguanide-based chemicals, aldehydes, and the like have been put to practical use as chemical methods, aside from such physical methods as heat and radiation. However, there is no product that is satisfactory in all respects, such as a good bactericidal effect, safety, low toxicity, excellent stability and shelf life, and low price. For instance, a biguanide-based chemical sold under the trade name Hibitane is an excellent, best-selling antiseptic, but it is ineffective against spores. Also, resistance has been noted in some bacteria, and this is known to be a cause of hospital acquired infection. There is no need to mention antibiotics, and as for chemical synthetics that are discomforting to microbial cells, resistant strains that render these ineffective always appear as a result of the production of enzymes or the production of substitute enzymes, and these are once again showing up as a threat to humans.

It is already known that certain types of metal ions have a bactericidal action over a specific concentration, and these have been applied in mercury preparations and the like. Mercury, however, is a heavy metal that is completely unnecessary in the body, and furthermore it is extremely toxic, so it has yielded its position as an antiseptic as the various antiseptics mentioned above have been developed, and ever since then antiseptics that make use of metal ions have been virtually ignored. More recently, metal elements have been recognized as essential substances in the body, and their dark image, first as poisons or alchemy and then as environmental pollutants in more recent years, has been swept away, until they are now considered one of the important elements that protect our health, with various minerals and tablets containing these being crowded together with foodstuffs in American supermarkets and the like.

Various metal ions were tested for their bactericidal effect on the major pathogenic bacteria, with the upper limit of the metal ion concentration set at 1000 ppm and the concentration set so as to exhibit the highest efficacy. The test method involved adding a suspension of sample bacteria ($1 \times 10^9$ cells/mL physiological saline) in an amount of 2 wt % to a metal ion solution, allowing 60 minutes for the contact time with the bacteria, sampling 10 $\mu$L of the treated liquid, culturing the samples in the optimal environment for each type of bacteria, and observing the viability of the bacteria. As a result, the same efficacy was exhibited, with the exception of spore forming bacteria. For the test, methicillin resistant Staphylococcus aureus (MRSA) was selected from among staphylococci as a typical Gram-positive bacterium, and *Escherichia coli* O-157 was selected from among *Escherichia coli* as a typical Gram-negative bacterium. These test results are given in Table 1. As is seen in Table 1, bactericidal action was noted for cupric ions ($CU^{2+}$) and ferric ions ($Fe^{3+}$). Viability of the bacteria was expressed as ++ when the bacteria proliferated normally with no impediment whatsoever, as + when they were damaged and their proliferation was somewhat inhibited, as ± when they were damaged and their proliferation was inhibited, and as − when they did not proliferate and were eradicated.

TABLE 1

Bactericidal action of various metal ions

| Metal ion | Compound name | Viability MRSA | O-157 |
|---|---|---|---|
| $Cu^{2+}$ | $CuSO_4.5H_2O$ | − | − |
| $Zn^{2+}$ | $ZnSO_4.7H_2O$ | + | − |
| $Mn^{2+}$ | $MnSO_4.5H_2O$ | ++ | ++ |
| $Co^{2+}$ | $CoCl_2.2H_2O$ | ++ | ++ |
| $Ni^{2+}$ | $NiSO_4.6H_2O$ | + | + |
| $Li^+$ | $Li_2SO_4.H_2O$ | ++ | ++ |
| $Ca^{3+}$ | $CaCl_2.2H_2O$ | ++ | ++ |
| $Mg^{2+}$ | $MgSO_4.7H_2O$ | ++ | ++ |
| $Si^{4+}$ | $SiO_2$ | ++ | ++ |
| $Rb^+$ | $Rb_2SO_4$ | ++ | ++ |
| $Al^{3+}$ | $Al_2(SO_4)_2.12H_2O$ | + | + |
| $Fe^{2+}$ | $FeCl_2$ | + | + |
|  | $FeCl_2.4H_2O$ | + | + |
|  | $Fe(CH_3CHOHCOO)_2.3H_2O$ | + | + |
|  | $FeC_2O_4.2H_2O$ | + | + |
|  | $FeSO_4.7H_2O$ | + | + |
| $Fe^{3+}$ | $FeCl_3$ | − | − |
|  | $FeCl_3.6H_2O$ | − | − |
|  | $Fe(NO_3)_3.9H_2O$ | − | − |
|  | $Fe_2(SO_4)_3.nH_2O$ | − | − |
|  | $FeC_6H_5O_7.nH_2O$ | − | − |
|  | $FePO_4.nH_2O$ | − | − |

Next, if we examine the relation between concentration and bacterium contact time for the bactericidal effect of ferric ions ($Fe^{3+}$), we see that an effect is gradually exhibited from 400 ppm upward, as shown in Table 2, and at 1000 ppm an effect is exhibited at a bacterium contact time of 5 minutes. The viability of the bacteria was evaluated the same as in Table 1.

TABLE 2

Bactericidal action of ferric ions ($Fe^{3+}$)

| Concentration as $Fe^{3+}$ (ppm) | Contact time with bacteria | Viability MRSA | O-157 |
|---|---|---|---|
| 100 | 10 seconds | ++ | ++ |
|  | 1 minute | ++ | ++ |
|  | 5 minutes | ++ | ++ |
| 200 | 10 seconds | ++ | ++ |
|  | 1 minute | ++ | ++ |
|  | 5 minutes | ++ | ++ |
| 400 | 10 seconds | ++ | ++ |
|  | 1 minute | ++ | ++ |
|  | 5 minutes | + | ± |
| 800 | 10 seconds | + | + |
|  | 1 minute | + | ± |
|  | 5 minutes | ± | − |
| 1000 | 10 seconds | + | ± |
|  | 1 minute | + | ± |
|  | 5 minutes | ± | − |

Meanwhile, the bactericidal action of sorbic acid, calcium sorbate, benzoic acid, sodium benzoate, and other such compounds known as food preservatives was examined. The concentration was 1000 ppm, and the contact time with the bacteria was 5 to 120 minutes, after which 10 μL of treated liquid was sampled and cultured in the optimal environment for each type of bacteria, and the viability of the bacteria was observed. As shown in Table 3, the test results for methicillin resistant Staphylococcus aureus (MRSA) and *Escherichia coli* O-157 indicated no bactericidal action in a short time, and when the contact time was extended to between 30 and 60 minutes, there was finally a bacteriostatic action or bacterial action. Viability of the bacteria was expressed as ++ when the bacteria proliferated normally with no impediment whatsoever, as + when they were damaged and their proliferation was somewhat inhibited, as ± when they were damaged and their proliferation was inhibited, as (−) when the coloring of the bacteriostatic action was darker than that of the bactericidal action, and as − when they did not proliferate and were eradicated.

TABLE 3

Bactericidal action of food preservatives

| Food preservative | Contact time with bacteria | Viability MRSA | O-157 |
|---|---|---|---|
| sorbic acid | 5 minutes | ++ | + |
|  | 15 | + | + |
|  | 30 | (−) | (−) |
|  | 60 | (−) | (−) |
|  | 120 | (−) | (−) |
| calcium sorbate | 5 minutes | ++ | ++ |
|  | 15 | + | + |
|  | 30 | ± | (−) |
|  | 60 | (−) | (−) |
|  | 120 | (−) | (−) |
| benzoic acid | 5 minutes | ++ | ++ |
|  | 15 | + | + |
|  | 30 | (−) | (−) |
|  | 60 | (−) | (−) |
|  | 120 | (−) | (−) |
| sodium benzoate | 5 minutes | ++ | ++ |
|  | 15 | + | + |
|  | 30 | ± | ± |
|  | 60 | (−) | (−) |
|  | 120 | (−) | (−) |

Pathogenic bacteria have long posed a threat to mankind, and it has been a goal in the food industry and the medical profession to develop a bactericide that would have a high degree of practicality which included spores in its scope, that would exhibit a pronounced effect on pathogenic bacteria, that would be safe for humans and the earth, and that would be composed of metal ions having affinity with the body, that is, those which are essential structural components for the body, and compounds that are used in food additives.

SUMMARY OF THE INVENTION

As a result of obtaining as many different water-soluble compounds of metal ions as possible, with the exception of harmful heavy metals that are unnecessary in the body, and investigating the bactericidal effect thereof, the inventors arrived at providing a metal ion-containing bactericide. Specifically, this is a bactericide containing ferric ions ($Fe^{3+}$) and one or more members of the group consisting of sorbic acid, benzoic acid, and para-hydroxybenzoic acid esters. It is preferable for the concentration of ferric ions ($Fe^{3+}$) to be 500 to 1500 ppm, and it is also preferable for the concentration of the one or more members of the group consisting of sorbic acid, benzoic acid, and para-hydroxybenzoic acid esters to be 200 to 2000 ppm.

The second present invention is a bactericide containing ferric ions ($Fe^{3+}$), L-ascorbic acid, and one or more members of the group consisting of sorbic acid, benzoic acid, and para-hydroxybenzoic acid esters. It is preferable for the concentration of ferric ions ($Fe^{3+}$) to be 500 to 1500 ppm, it is preferable for the concentration of L-ascorbic acid to be 500 to 2000 ppm, and it is also preferable for the concentration of the one or more members of the group consisting of sorbic acid, benzoic acid, and para-hydroxybenzoic acid esters to be 200 to 2000 ppm.

The third present invention is a bactericide containing ferric ions ($Fe^{3+}$), sorbic acid, benzoic acid, and L-ascorbic acid. It is preferable for the concentration of the ferric ions ($Fe^{3+}$) to be 500 to 1500 ppm, the concentration of the sorbic acid and benzoic acid to be 200 to 2000 ppm, and the concentration of the L-ascorbic acid to be 500 to 2000 ppm.

Figure 1:
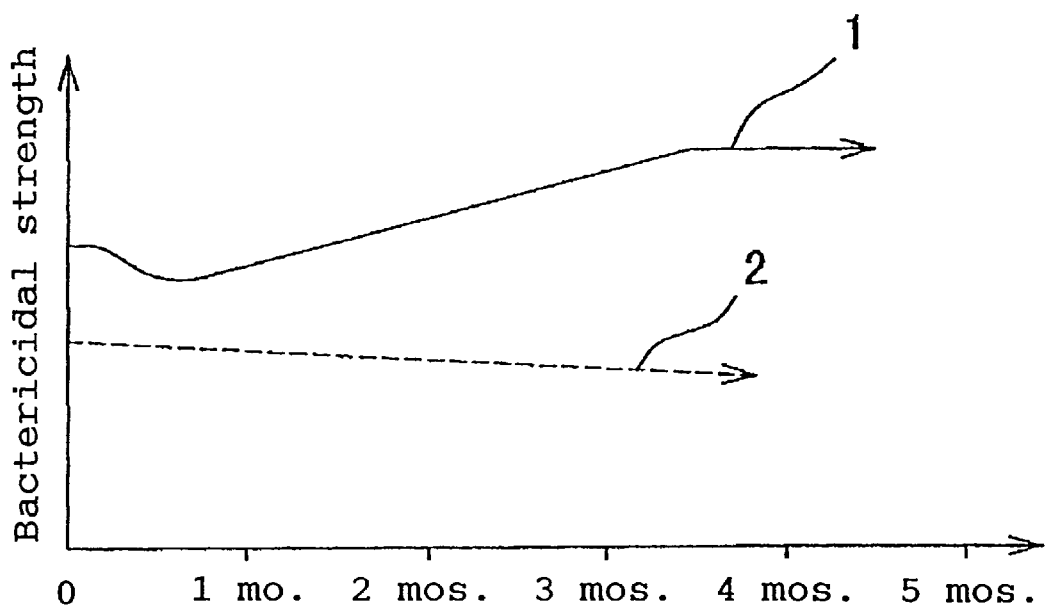
FIG. 1 is a comparison of the changes in bactericidal strength.

Key:

1: Change in the bactericidal strength of the iron ion-containing bactericide of the present invention 2: Change in the bactericidal strength of a conventional antiseptic

DESCRIPTION OF THE PREFERRED EMBODIMENTS

The phrase "ferric ions ($Fe^{3+}$)" used in the present invention means that $Fe^{3+}$ ions are present in a solution, which can be obtained, for example, by dissolving ferric chloride, ferric chloride hexahydrate, ferric nitrate, ferric nitrate hexahydrate, ferric nitrate nonahydrate, ferric sulfate n-hydrate, ferric phosphate n-hydrate, ferric citrate n-hydrate, or the like in water.

The sorbic acid referred to in the present invention is not only sorbic acid itself, but also includes sorbates, examples of which include potassium sorbate and sodium sorbate.

The benzoic acid referred to in the present invention is not only benzoic acid itself, but also includes benzoates, examples of which include potassium benzoate, sodium benzoate, calcium benzoate, ammonium benzoate, and zinc benzoate.

The para-hydroxybenzoic acid ester referred to in the present invention is an ester of para-hydroxybenzoic acid and an alcohol, examples of which include methyl para-hydroxybenzoate, ethyl para-hydroxybenzoate, butyl para-hydroxybenzoate, and propyl para-hydroxybenzoate.

The pathogenic bacteria referred to in the present invention are microbes that are the cause of disease, such as bacteria or viruses to cause enteric canal infection, respiratory organ infection, ureter infection, etc. Examples of bacteria that cause various infectious diseases include Salmonella spp., Shigella spp., *Vibrio parahaemolyticus, Vibrio choreae, Escherichia coli* O-157, *Campylobacter jejuni, Clostridium difficile, Clostridium perfringens, Yersinia enterocolitica, Heliobacter pylori, Entemoea histolytica, Bacillus cereus,* Staphylococcus spp., *Clostridium botulinum, Haemophilus influenzae, Streptococcus pneumoniae, Chlamidia pneumoniae, Legionella pneumoniae, Branhamella catarrhalis, Mycobacterium tuberculosis, Mycoplasma pneumoniae, Streptococcus pyogenes, Corynebacterium diphtheriae, Bordetella pertussis, Chlamidia psittaci, Pseudomonas aerginosa,* methicillin resistant *Staphylococcus aureus* (MRSA), *Escherichia coli, Klebsiella pneumoniae,* Enterobacter spp., Proteus spp., Acinetobacter spp., *Enterococcus faecalis, Staphylococcus saprophyticus,* and *Streptococcus agalactiae*.

Antisepsis as used in the present invention means eradicating pathogenic bacteria, and is not concerned with the survival of non-pathogenic microorganisms. In this respect, disinfection means completely killing all microorganisms, not just pathogenic microorganisms. Therefore, an antiseptic refers to a chemical substance when sterilization is performed with this chemical substance.

The mechanism of action of the iron ion-containing bactericide of the present invention is not fully understood as yet, but is believed to be as follows. Iron is an essential substance for all organisms, and the iron in food is present in the form of inorganic iron (a complex in which ferric ions are bonded to an amino acid or a peptide), heme iron bonded to animal protein, or nonheme iron bonded to vegetable protein. This iron bonds with as many as 200 different types of enzymes in the body and supports vital activities. It is also responsible for $O_2$ transport as the main component of hemoglobin. Thus, ferric ions ($Fe^{3+}$) is an active form that is far more powerful in the body than ferrous ions ($Fe^{2+}$), and also has more powerful oxidation. In higher organisms, iron undergoes orderly bonding with predetermined enzymes under command, but in single-celled organisms, the osmotic action is further increased by the above-mentioned fortifiers or the like, quickly penetrating into the cell from the outside, and the filling $Fe^{3+}$ ions can eventually upset the system, bonding to enzymes and proteins in an avalanche, which can be fatal to a bacterium. The powerful oxidizing action thereof is also thought to destroy cellular walls and the like in an extremely short time, as if they were being attacked.

The bactericidal strength of the iron ion-containing bactericide of the present invention can be enhanced by the addition of a minute amount of cupric ions ($Cu^{2+}$), zinc ions ($Zn^2e$), an extract containing any of various metal ions and having mica as a raw material, an antibiotic substance derived from any of various plants (specifically, a substance called a phytoncide; the essential oils of plants primarily correspond to this, such as tea tree oil, thymol, camphor, clove, chamomile, eucalyptus, oregano, and other such essential oils), a plant extract containing any of various minerals, a surfactant, or the like.

EXAMPLES

The iron ion-containing bactericide of the present invention is produced by dissolving a compound composed of ferric ions ($Fe^{3+}$) in water and then preparing a solution of benzoic acid or a benzoate. Also, sorbic acid or a sorbate is dissolved in water to prepare an aqueous solution of sorbic acid. Meanwhile, L-ascorbic acid is dissolved in water to prepare an aqueous solution of L-ascorbic acid. These aqueous solutions are mixed as dictated by the composition of the bactericide to manufacture an iron ion-containing bactericide. The present invention will now be described in further detail through examples, but the gist of the present invention is not limited to or by these examples.

Example 1

For ferric chloride hexahydrate ($FeCl_3.6H_2O$) as the ferric ions ($Fe^{3+}$), methicillin resistant *Staphylococcus aureus* (MRSA) was selected from among staphylococci, *Escherichia coli* O-157 was selected from among *Escherichia coli*, the concentration of ferric ions ($Fe^{3+}$) was set between 500 and 2000 ppm, the concentrations of sorbic acid or benzoic acid were set between 100 and 2500 ppm, and the bacterium contact time was set between 10 seconds and 5 minutes, after which the bactericidal action was tested. The test method involved adding a suspension of sample bacteria ($1 \times 10^9$ cells/mL physiological saline) in an amount of 2 wt % to an iron ion-containing bactericide, allowing a specific amount of time for contact with the bacteria, sampling 10 µL of the treated liquid, culturing the sample in the optimal environment for each type of bacteria, and observing the viability of the bacteria. These results are given in Tables 4 and 5, which show that both MRSA and *E. coli* O-157 were eradicated at a contact time of only 10 seconds with a mixed liquid having an ferric ion ($Fe^{3+}$) concentration of 1000 ppm and a sorbic acid concentration of 1000 ppm. A similar bactericidal effect was obtained with potassium sorbate, benzoic acid, and sodium benzoate. Viability of the bacteria was expressed as ++ when the bacteria proliferated normally with no impediment whatsoever, as + when they were damaged and their proliferation was somewhat inhibited, as ± when they were damaged and their proliferation was inhibited, and as – when they did not proliferate and were eradicated.

TABLE 4

Bactericidal action using both ferric ions ($Fe^{3+}$) and food preservatives (1)

| Concen. as $Fe^{3+}$ (ppm) | Food preservative Compound name | Concen. (ppm) | Viability MRSA 10 sec* | 1 min* | 5 min* | O-157 10 sec* | 1 min* | 5 min* |
|---|---|---|---|---|---|---|---|---|
| 500 | potassium sorbate | 100 | ++ | ++ | + | ++ | ++ | + |
|  |  | 200 | ++ | + | ± | ++ | + | ± |
|  |  | 500 | ++ | + | ± | ++ | + | ± |
|  |  | 1000 | ++ | + | ± | ++ | + | – |
|  |  | 1500 | ++ | + | – | ++ | ± | – |
|  |  | 2000 | ++ | ± | – | ++ | ± | – |
|  |  | 2500 | ++ | ± | – | ++ | ± | – |
|  | sodium benzoate | 100 | ++ | ++ | + | ++ | ++ | + |
|  |  | 200 | ++ | + | + | ++ | + | ± |
|  |  | 500 | ++ | + | ± | ++ | + | ± |
|  |  | 1000 | ++ | + | ± | ++ | + | – |
|  |  | 1500 | ++ | + | – | ++ | + | – |
|  |  | 2000 | ++ | ± | – | ++ | ± | – |
|  |  | 2500 | ++ | ± | – | ++ | ± | – |
| 1000 | potassium sorbate | 100 | + | ± | + | ± | + | – |
|  |  | 200 | + | ± | – | + | ± | – |
|  |  | 500 | ± | – | – | ± | – | – |
|  |  | 1000 | – | – | – | – | – | – |
|  |  | 1500 | – | – | – | – | – | – |
|  |  | 2000 | – | – | – | – | – | – |

TABLE 4-continued

Bactericidal action using both ferric ions ($Fe^{3+}$) and food preservatives (1)

| Concen. as $Fe^{3+}$ (ppm) | Food preservative Compound name | Concen. (ppm) | Viability MRSA 10 sec* | 1 min* | 5 min* | 0–157 10 sec* | 1 min* | 5 min* |
|---|---|---|---|---|---|---|---|---|
| | | 2500 | – | – | – | – | – | – |
| | sodium benzoate | 100 | + | + | ± | + | ± | – |
| | | 200 | + | ± | – | ± | ± | – |
| | | 500 | ± | – | – | ± | – | – |
| | | 1000 | – | – | – | ± | – | – |
| | | 1500 | – | – | – | – | – | – |
| | | 2000 | – | – | – | – | – | – |
| | | 2500 | – | – | – | – | – | – |
| | sorbic acid | 100 | + | + | ± | + | ± | – |
| | | 200 | + | ± | – | + | ± | – |
| | | 500 | ± | – | – | ± | – | – |
| | | 1000 | – | – | – | – | – | – |
| | | 1500 | – | – | – | – | – | – |
| | | 2000 | – | – | – | – | – | – |
| | | 2500 | – | – | – | – | – | – |

*Contact time with bactericide.

TABLE 5

Bactericidal action using both ferric ions ($Fe^{3+}$) and food preservatives (2)

| Concen. as $Fe^{3+}$ (ppm) | Food preservative Compound name | Concen. (ppm) | Viability MRSA 10 sec* | 1 min* | 5 min* | 0–157 10 sec* | 1 min* | 5 min* |
|---|---|---|---|---|---|---|---|---|
| 1500 | potassium sorbate | 100 | + | ± | ± | + | ± | – |
| | | 200 | + | ± | – | + | ± | – |
| | | 500 | ± | – | – | – | – | – |
| | | 1000 | – | – | – | – | – | – |
| | | 1500 | – | – | – | – | – | – |
| | | 2000 | – | – | – | – | – | – |
| | | 2500 | – | – | – | – | – | – |
| | sodium benzoate | 100 | + | ± | ± | + | ± | – |
| | | 200 | + | ± | – | + | ± | – |
| | | 500 | ± | – | – | ± | – | – |
| | | 1000 | – | – | – | – | – | – |
| | | 1500 | – | – | – | – | – | – |
| | | 2000 | – | – | – | – | – | – |
| | | 2500 | – | – | – | – | – | – |
| | benzoic acid | 100 | + | ± | ± | + | ± | – |
| | | 200 | + | ± | – | + | ± | – |
| | | 500 | ± | – | – | ± | – | – |
| | | 1000 | – | – | – | – | – | – |
| | | 1500 | – | – | – | – | – | – |
| | | 2000 | – | – | – | – | – | – |
| | | 2500 | – | – | – | – | – | – |
| 2000 | sodium sorbate | 100 | + | ± | ± | + | ± | – |
| | | 200 | + | ± | – | + | ± | – |
| | | 500 | ± | – | – | ± | – | – |
| | | 1000 | – | – | – | – | – | – |
| | | 1500 | – | – | – | – | – | – |
| | | 2000 | – | – | – | – | – | – |
| | | 2500 | – | – | – | – | – | – |
| | sodium benzoate | 100 | + | ± | ± | + | ± | – |
| | | 200 | + | ± | ± | ± | ± | – |
| | | 500 | ± | – | – | ± | – | – |
| | | 1000 | – | – | – | – | – | – |
| | | 1500 | – | – | – | – | – | – |
| | | 2000 | – | – | – | – | – | – |
| | | 2500 | – | – | – | – | – | – |

*Contact time with bactericide.

Example 2

For ferric chloride hexahydrate as the ferric ions ($Fe^{3+}$), just as in Example 1, methicillin resistant *Staphylococcus aureus* (MRSA) and *Escherichia coli* O-157 were selected, the concentration of ferric ions ($Fe^{3+}$) was set at 1000 ppm, the concentrations of sorbic acid or benzoic acid were set between 50 and 500 ppm, and the bacterium contact time was set between 10 seconds and 5 minutes, after which the bactericidal action was tested. The test was conducted in the same manner as in Example 1, and the viability of the bacteria was observed. These results are given in Table 6, which shows that an excellent bactericidal effect is exhibited when the ferric ion ($Fe^{3+}$) concentration is at least 500 ppm, and preferably 500 to 1500 ppm, and the sorbic acid and benzoic acid are contained, either alone or combined, in an amount of at least 200 ppm, and preferably 200 to 2000 ppm.

TABLE 6

Bactericidal action using both ferric ions ($Fe^{3+}$) and food preservatives (3)

| Concen. as $Fe^{3+}$ (ppm) | Food preservative combination Compound name | Concen. (ppm) | Viability MRSA 10 sec* | 1 min* | 5 min* | 0–157 10 sec* | 1 min* | 5 min* |
|---|---|---|---|---|---|---|---|---|
| 1000 | potassium sorbate | 50 | + | + | – | + | ± | – |
| | sodium benzoate | 50 | | | | | | |
| | potassium sorbate | 100 | + | ± | – | + | ± | – |
| | sodium benzoate | 100 | | | | | | |
| | potassium sorbate | 50 | + | ± | – | + | ± | – |
| | sodium benzoate | 50 | | | | | | |
| | sorbic acid | 100 | | | | | | |
| | potassium sorbate | 200 | ± | – | – | ± | – | – |
| | sodium benzoate | 300 | | | | | | |
| | potassium sorbate | 200 | – | – | – | – | – | – |
| | sodium benzoate | 300 | | | | | | |
| | sorbic acid | 500 | | | | | | |
| | potassium sorbate | 250 | – | – | – | – | – | – |
| | sodium benzoate | 250 | | | | | | |
| | sorbic acid | 250 | | | | | | |
| | benzoic acid | 250 | | | | | | |

*Contact time with bactericide.

Comparative Example 1

Using ferrous chloride and ferrous sulfate heptahydrate as ferrous ions ($Fe^{2+}$) instead of the ferric chloride hexahydrate used in Example 1, methicillin resistant *Staphylococcus aureus* (MRSA) and *Escherichia coli* O-157 were selected, the concentration of ferrous ions ($Fe^{2+}$) was set at 1000 ppm, the concentrations of sorbic acid or benzoic acid were set at 1000 ppm, and the bacterium contact time was set between 10 and 30 minutes, after which the bactericidal action was tested. The test was conducted in the same manner as in Example 1, and the viability of the bacteria was observed. These results are given in Table 7, which shows that even sorbic acid or benzoic acid was added, when the ferrous ion ($Fe^{2+3}$) concentration was 1000 ppm, neither the MRSA nor the *E. coli* O-157 was erradicated within a contact time of 20 minutes.

TABLE 7

Bactericidal action of ferrous ions ($Fe^{2+}$)

| $Fe^{2+}$ compound name (concen. as $Fe^{2+}$: 1000 ppm) | Food preservative name (concen.: 1000 ppm) | Contact time with bacteria | Viability MRSA | O-157 |
|---|---|---|---|---|
| Ferrous chloride ($FeCl_2$) | none added | 10 | ++ | ++ |
| | | 20 | ++ | ++ |
| | | 30 | ++ | ++ |
| | potassium sorbate | 10 | ++ | ++ |
| | | 20 | + | ± |
| | | 30 | − | − |
| | sodium benzoate | 10 | ++ | ++ |
| | | 20 | + | ± |
| | | 30 | (−) | − |
| Ferrous sulfate ($FeSO_4.7H_2O$) | none added | 10 | ++ | ++ |
| | | 20 | ++ | ++ |
| | | 30 | ++ | ++ |
| | potassium sorbate | 10 | ++ | ++ |
| | | 20 | + | ± |
| | | 30 | − | − |
| | sodium benzoate | 10 | ++ | ++ |
| | | 20 | + | ± |
| | | 30 | (−) | − |

Comparative Example 2

Bactericidal action was tested by the same method as in Example 1 for carbolic acid, aqueous hydrogen peroxide, and a Hibitane solution containing 5% chlorhexidine gluconate ($C_{22}H_{30}ClN_{10}.2C_6H_{12}O_7$). These results are given in Table 8, which shows that a bactericidal effect is not exhibited at a bacterium contact time of 10 seconds even at a high concentration of 30,000 ppm.

TABLE 8

Bactericidal action of antiseptics

| Antiseptic (ppm) | Contact time with bacteria | Viability MRSA | O-157 |
|---|---|---|---|
| Carbolic acid | | | |
| 3000 | 10 sec | ++ | ++ |
| | 1 min | ++ | ++ |
| | 5 min | ++ | ++ |
| 10,000 | 10 sec | ++ | ++ |
| | 1 min | ++ | ++ |
| | 5 min | + | + |
| 30,000 | 10 sec | ± | ± |
| | 1 min | − | − |
| | 5 min | − | − |
| Aqueous hydrogen peroxide | | | |
| 3000 | 10 sec | ++ | ++ |
| | 1 min | ++ | ++ |
| | 5 min | + | − |
| 10,000 | 10 sec | + | ++ |
| | 1 min | ± | ± |
| | 5 min | − | − |
| 30,000 | 10 sec | ± | + |
| | 1 min | − | − |
| | 5 min | − | − |
| Hibitane solution | | | |
| 3000 | 10 sec | ++ | ++ |
| | 1 min | ++ | ++ |
| | 5 min | + | + |
| 10,000 | 10 sec | ++ | ++ |
| | 1 min | + | + |
| | 5 min | ± | ± |
| 30,000 | 10 sec | + | + |
| | 1 min | − | − |
| | 5 min | − | − |

Example 3

An aqueous solution of ferric chloride hexahydrate with a concentration of 2000 ppm as $Fe^{3+}$ was prepared, then an aqueous solution of 2000 ppm potassium sorbate was made, and these aqueous solutions were mixed in amounts of 1 liter each to prepare 2 liters of bactericide containing iron ions. This solution therefore contained 1000 ppm each of $Fe^{3+}$ and potassium sorbate. Daikon [white radish] sprouts to which numerous *E. coli* O-157 had adhered was dipped in this 2 L solution and left for 1 hour, after which the radish sprouts and the used bactericide were checked for *E. coli* O-157, but no bacteria could be detected.

Example 4

5 g of ferric sulfate [$Fe_2(SO_4)_3.nH_2O$)] and 1 g of sodium benzoate were dissolved in 1 L of water $Fe^{3+} \approx 1000$ ppm; sodium benzoate=1000 ppm) to prepare a bactericide containing iron ions. The hands of a test subject were thoroughly washed with this bactericide for 10 seconds, after which the hands were tested for bacteria, but nothing was detected other than spores of the Bacillus genus.

Example 5

L-ascorbic acid was added to an iron ion-containing bactericide of ferric chloride hexahydrate and potassium sorbate and to an iron ion-containing bactericide of ferric chloride hexahydrate and sodium benzoate, and the time it took to eradicate spores was tested for 50 species of spores from the Bacillus genus and 50 species of spores from the Clostridium genus. The effect of a surfactant was also examined at this time. Here, solution A contained 1000 ppm (as $Fe^{3+}$) ferric chloride and 500 ppm potassium sorbate; solution B contained 1000 ppm (as $Fe^{3+}$) ferric chloride and 500 ppm sodium benzoate; solution C contained 1000 ppm (as $Fe^{3+}$) ferric chloride, 500 ppm potassium sorbate, and 1000 ppm ascorbic acid; solution D contained 1000 ppm (as $Fe^{3+}$) ferric chloride, 500 ppm sodium benzoate, and 1000 ppm ascorbic acid; solution E contained 1000 ppm (as $Fe^3$) ferric chloride, 500 ppm potassium sorbate, 1000 ppm ascorbic acid, and 100 ppm sodium laurylsulfate; and solution F contained 1000 ppm (as $Fe^{3+}$) ferric chloride, 500 ppm potassium sorbate, 1000 ppm ascorbic acid, and 50 ppm tea tree oil. These results are given in Table 9, which shows that the eradication of spores did not go over 50% even after 120 minutes of bacterium contact with the bactericides to which no L-ascorbic acid was added. However, with the bactericides to which L-ascorbic acid was added, there were spores that were eradicated at a bacterium contact time of 5 minutes, 92 to 98% of the spores were eradicated after 120 minutes of contact, and when a small amount of surfactant was added, there were bacteria that were eradicated after contact of only 1 minute, and all of the spores had been eradicated by 120 minutes of contact. Meanwhile, with the Hibitane solution used in the past, there were no spores eradicated even after 120 minutes of contact, and only 20 to 24% of the spores were eradicated by aqueous hydrogen peroxide.

of 20 test tubes was filled with 10 mL of this bactericide. Dry earth and sand containing numerous spores from the Bacillus and Clostridium genera were sampled from 20 sites, and 0.2 g of each was added to the bactericide in the above-mentioned test tubes. These were allowed to stand for 120 minutes, after which the used bactericides were checked for bacteria, but no spores of either the Bacillus genus or the Clostridium genus were detected, let alone any ordinary

TABLE 9

Time required for bacteria to die, and proportion thereof

|  |  | Bacillus spores, 50 species | | | | | | Clostridium spores, 50 species | | | | | |
| --- | --- | --- | --- | --- | --- | --- | --- | --- | --- | --- | --- | --- | --- |
|  |  | 10 sec | 1 min | 5 min | 30 min | 60 min | 120 min | 10 sec | 1 min | 5 min | 30 min | 60 min | 120 min |
| Present invention bactericide | A | 0 | 0 | 4 | 20 | 40 | 50% | 0 | 0 | 6 | 16 | 30 | 40% |
|  | B | 0 | 0 | 4 | 18 | 36 | 44% | 0 | 0 | 6 | 14 | 26 | 34% |
|  | C | 0 | 0 | 12 | 38 | 72 | 98% | 0 | 0 | 14 | 32 | 50 | 96% |
|  | D | 0 | 0 | 12 | 34 | 68 | 92% | 0 | 0 | 12 | 38 | 46 | 92% |
|  | E | 0 | 4 | 26 | 72 | 90 | 100% | 0 | 2 | 20 | 52 | 72 | 100% |
|  | F | 0 | 2 | 12 | 42 | 80 | 100% | 0 | 6 | 18 | 48 | 76 | 100% |
| Ordinary bactericide | Hibitane | 0 | 0 | 0 | 0 | 0 | 0% | 0 | 0 | 0 | 0 | 0 | 0% |
|  | $H_2O_2$ | 0 | 0 | 0 | 2 | 10 | 20% | 0 | 0 | 0 | 4 | 12 | 24% |

Example 6

An aqueous solution of ferric chloride ($FeCl_3$) with a concentration of 2400 ppm as $Fe^{3+}$, an aqueous solution of L-ascorbic acid with a concentration of 3000 ppm, and an aqueous solution of sorbic acid with a concentration of 600 ppm were prepared, and these three types of aqueous solution were mixed in equal amounts to prepare a bactericide containing iron ions. 0.1 g of sodium laurate was added to 1 L of this bactericide. A dinner plate to which leftover food had adhered and which had been allowed to stand overnight was lightly washed as usual with this bactericide, whereupon the food came right off, without any neutral detergent, and furthermore no bacteria were detected on the plate.

Example 7

An aqueous solution of ferric chloride hexahydrate with a concentration of 3000 ppm as $Fe^{3+}$, an aqueous solution of L-ascorbic acid with a concentration of 2400 ppm, and an aqueous solution of sorbic acid with a concentration of 1500 ppm were prepared, and these three types of aqueous solution were mixed in equal amounts to prepare a bactericide containing iron ions. A rotting piece of pork was dipped in this bactericide for 1 minute, after which the liquid was thoroughly wiped off with a piece of sterile gauze and applied to an agar culture medium. This was cultured at 28° C. and 37° C., whereupon no bacteria proliferated in either medium, and it was confirmed that all of the countless putrefying bacteria that had been proliferating on the pork were eradicated in just one minute.

Example 8

An aqueous solution of ferric nitrate nonahydrate [$Fe(NO_3)_3 \cdot 9H_2O$] with a concentration of 3000 ppm as $Fe^{3+}$, an aqueous solution of L-ascorbic acid with a concentration of 3000 ppm, and an aqueous solution of sodium benzoate with a concentration of 900 ppm were prepared, and these three types of aqueous solution were mixed in equal amounts to prepare a bactericide containing iron ions. Each bacteria, in 19 of the test tubes. However, the presence of 12 spores per mL of bactericide was detected in the remaining tube.

The strength of an antiseptic or bactericide is generally highest immediately after its manufacture, and declines gradually as time passes. Nevertheless, as a result of the addition of L-ascorbic acid, the iron ion-containing bactericide of the present invention is at its most powerful several months after its manufacture, as shown in FIG. 1, with a stable bactericidal strength being maintained over an extended period. Also, as to color, the bactericide changes into a solution that appears colorless and transparent.

Effect of the Invention

The iron ion-containing bactericide of the present invention has as its components ferric ions, which are structural elements of the body, and compounds approved for use as food additives, and is therefore highly stable and can be used in a wide range of applications, from the sterilization of hands and wounds, to the sterilization of furniture, tools, and objects, to the sterilization of fresh foods prior to cooking. Also, the major pathogenic bacteria, such as MRSA or *E. coli* O-157 can be killed in about 10 seconds of contact with the bactericide, and even over 90% of spores can be killed at a contact time of 120 minutes. Furthermore, this bactericide has many advantages not found in conventional antiseptics, such as an effect that is stable over extended periods, and is more convenient to use.

What is claimed is:

1. A bactericidal composition containing ferric ions ($Fe^{3+}$) having a concentration of from 500 to 1500 ppm, L-ascorbic acid having a concentration of from 500 to 2000 ppm, and one or more members having a concentration of from 200 to 2000 ppm of the group consisting of sorbic acid, benzoic acid, and para-hydroxybenzoic acid esters.

* * * * *